(12) United States Patent
Kalman et al.

(10) Patent No.: US 9,408,677 B2
(45) Date of Patent: Aug. 9, 2016

(54) DENTAL PROSTHESIS ABUTMENT SYSTEM AND METHOD FOR USING SAME

(76) Inventors: Laszlo Joseph Kalman, Kilworth (CA); Lina Kalman, Kilworth (CA)

( * ) Notice: Subject to any disclaimer, the term of this patent is extended or adjusted under 35 U.S.C. 154(b) by 0 days.

(21) Appl. No.: 12/668,832

(22) PCT Filed: Jul. 16, 2008

(86) PCT No.: PCT/CA2008/001312
§ 371 (c)(1),
(2), (4) Date: Jan. 12, 2010

(87) PCT Pub. No.: WO2009/009897
PCT Pub. Date: Jan. 22, 2009

(65) Prior Publication Data
US 2010/0190135 A1    Jul. 29, 2010

(51) Int. Cl.
  *A61C 13/12* (2006.01)
  *A61C 8/00* (2006.01)
  *A61C 13/107* (2006.01)
  *A61C 13/00* (2006.01)

(52) U.S. Cl.
  CPC .............. *A61C 8/005* (2013.01); *A61C 13/0001* (2013.01); *A61C 13/0003* (2013.01); *A61C 8/0054* (2013.01); *A61C 8/0072* (2013.01)

(58) Field of Classification Search
  CPC ...... A61C 8/008; A61C 8/005; A61C 8/0068; A61C 8/0066; A61C 8/0069; A61C 8/0048
  USPC ................................. 433/169–174, 177, 201.1
  See application file for complete search history.

(56) References Cited

U.S. PATENT DOCUMENTS

| | | | | |
|---|---|---|---|---|
| 2,880,508 A | * | 4/1959 | Lester et al. | 433/169 |
| 3,656,236 A | * | 4/1972 | Kurer | 433/221 |
| 4,193,194 A | * | 3/1980 | Dalise | 433/177 |
| 4,531,916 A | | 7/1985 | Scantlebury et al. | |
| 4,552,532 A | * | 11/1985 | Mozsary | 433/173 |
| 4,744,756 A | * | 5/1988 | Ross | 433/173 |
| 5,073,111 A | | 12/1991 | Daftary | |
| 5,145,372 A | | 9/1992 | Daftary et al. | |

(Continued)

FOREIGN PATENT DOCUMENTS

| | | |
|---|---|---|
| CA | 2526318 | 11/2005 |
| EP | 0630621 | 12/1994 |

(Continued)

OTHER PUBLICATIONS

"RN synOcto temporary meso abutment," Straumann Canada limited, Burlington, Ontario Canada, 7 pp., Jan. 30, 2006.

(Continued)

*Primary Examiner* — Yogesh Patel (57) ABSTRACT

A dental abutment system permitting to limit the steps and time required for a dental implant procedure. The dental abutment system (10) comprises a cap (12) coupled to a retentive member (14) that is coupled to a sheath (16). The cap (12) has a shaft (18) for coupling with a bore (24) of a dental implant (20) and the sheath (16) is coupled to the bore (24) of a dental prosthesis (26) such that the dental prosthesis (26) is frictionally retained to and removable from the cap (12). The retentive member (14) may include an area-of-weakness permitting it to break-away from the cap (12) to avoid the transmission of excessive forces to the implant (20).

23 Claims, 7 Drawing Sheets

(56) References Cited

U.S. PATENT DOCUMENTS

| | | | |
|---|---|---|---|
| 5,458,488 A * | 10/1995 | Chalifoux | 433/173 |
| 5,527,183 A * | 6/1996 | O'Brien | 433/174 |
| 5,571,016 A * | 11/1996 | Ingber et al. | 433/173 |
| 5,651,675 A | 7/1997 | Singer | |
| 5,989,026 A | 11/1999 | Rogers et al. | |
| 6,152,737 A | 11/2000 | Beaty et al. | |
| 6,171,106 B1 | 1/2001 | Kaneko et al. | |
| 6,247,933 B1 * | 6/2001 | Wagner et al. | 433/173 |
| 6,283,753 B1 * | 9/2001 | Willoughby | 433/172 |
| 6,299,447 B1 * | 10/2001 | Zuest et al. | 433/172 |
| 6,306,143 B1 * | 10/2001 | Kvarnstrom et al. | 606/105 |
| 6,644,970 B1 * | 11/2003 | Lin | 433/173 |
| 6,716,030 B1 | 4/2004 | Bulard et al. | |
| 6,726,480 B1 * | 4/2004 | Sutter | 433/173 |
| 7,300,282 B2 * | 11/2007 | Sapian | 433/173 |
| 2002/0150862 A1 | 10/2002 | Day | 433/173 |
| 2004/0209227 A1 * | 10/2004 | Porter et al. | 433/173 |
| 2005/0037319 A1 * | 2/2005 | Bulard et al. | 433/173 |
| 2005/0233281 A1 * | 10/2005 | Gittleman | 433/173 |
| 2008/0118892 A1 * | 5/2008 | Adams | 433/174 |

FOREIGN PATENT DOCUMENTS

| | | |
|---|---|---|
| ES | 2197743 | 2/2005 |
| JP | 05197757 | 7/1993 |
| JP | 2002005393 | 1/2002 |
| JP | 2004337190 | 12/2004 |
| JP | 2005168874 | 6/2005 |
| RU | 2146901 | 3/2000 |
| WO | WO2006/065213 | 6/2006 |

OTHER PUBLICATIONS

International Search Report and Written Opinion dated Oct. 31, 2008 for corresponding international patent application No. PCT/CA08/01312.

Misch, C.E., Contemporary Implant Dentistry (2nd. ed.), Mosby, 1999, pp. 347-397.

Caplanis, N., et al., "Osseointegration: Contemporary concepts and treatment," CDA Journal, Dec. 1997, vol. 25, No. 12, pp. 69-76.

Arlin, M.L., "What Works in Implant Dentistry: An Analysis of 2,235 Implants Placed in a Private Periodontal Practice," Jan./Feb. 2000, pp. 39-49.

Zosky, J.G., et al., "Immediate Implant Placement and Immediate Load with an Acrylic Temporary Crown in the Aesthetic Zone: Two Case Reports," Dentaltown, vol. 7, Issue 9, pp. 6-13.

Misch, C.E "Wide-Diameter Implants: Surgical, Loading, and Prosthetic Considerations," Oral Health, Aug. 2006, 5 pages.

* cited by examiner

DENTAL PROSTHESIS ABUTMENT SYSTEM AND METHOD FOR USING SAME

FIELD OF THE INVENTION

The present invention relates generally to dental implants, and more particularly, to a dental prosthesis abutment system associated with a dental prosthesis and a method for using same.

BACKGROUND OF THE INVENTION

Dental implants have existed for many years and have become the gold standard of dentistry. A clinician may recommend dental implants as a suggested method of replacing teeth.

An example of a standard procedure of placing and restoring dental implants consists of several stages. Initially, the procedure starts with the creation of an osteotomy or hole in the jaw bone. A titanium metal root analogue is then placed in the hole. A healing cap or a screw top is then coupled to the dental implant and 6-12 weeks is allowed to pass to permit osseointegration. During this period, a temporary partial denture is usually placed over the healing cap and dental implant. Following this period, the healing cap is removed and dental impressions are taken. The healing cap is then replaced over the dental implant for an additional 2-3 weeks after which the healing cap is removed. An abutment serving as the framework for a dental prosthesis is then permanently screwed onto the dental implant. During the final restoration, a permanent dental prosthesis is then cemented onto the abutment.

A typical healing cap is one component of a dental implant. The healing cap allows for a seal around the dental implant and prevents bacteria from entering around the dental implant. The healing cap may have a polished surface, which allows for the optimum healing of soft tissues surrounding the dental implant. This ultimately allows for maximum aesthetics.

The acceptance of dental implants has been hindered by many factors. Some of these may be due to complexity of the surgery and prosthetic phases, as well as the confusion associated with numerous components of dental implant systems. Patients may have difficulty with the cost of the dental implant treatment and/or avoid dental implant treatment to avoid the burden of having a temporary partial denture. Other than inconvenience, the temporary partial denture themselves may be the cause of several concerns and problems. Patients tend to have psychological issues associated with the implants and the temporary partial denture. For example, some issues comprise gagging, speech impediment, reduced aesthetics, and removability. In addition, food collection is commonly observed in these procedures which can cause infection and tissue inflammation.

Recent studies have indicated that a majority of dental implants can be introduced immediately; patients can have a dental implant surgically placed and a dental prosthesis restored for immediate function. An immediate restoration will guide the healing of the tissues and minimize the recession of the gum as well as maximize the aesthetic potential of the dental implant. An immediate restoration would also eliminate the need for the temporary partial denture. This potentially eliminates patient related psychological issues that may be associated with food collection and inflammation. The healing of soft tissue is also maximized based on this implant technique. Furthermore, because fewer reagents and steps are contemplated, there is an overall cost reduction of the dental implant procedure.

Straumann (Straumann Canada Ltd.) produces an abutment that can be placed onto a suitable dental implant. The abutment is called the RN synOcta® temporary meso abutment (RN abutment). The RN abutment has an acrylic extension that can be drilled and shaped to act as an abutment or fake tooth framework. Once the RN abutment has been shaped, it can now accept a crown as a temporary prosthesis. However, this design suffers many drawbacks. First, the RN abutment must be sandblasted or bonded for the crown or temporary dental prosthesis to adhere. Once the crown has been cemented, it cannot be removed from the RN abutment without causing some damage to the abutment or the crown. Furthermore, the RN abutment prevents the clinician from viewing the interface between the dental implant and healing cap to determine if a good seal has been achieved for the dental implant to osseointegrate. Without direct visual confirmation of the seating of the RN abutment, the clinician is left with the concern of whether or not the RN abutment has indeed been seated properly. Failure to adequately view the seating may compromise the success of the osseointegration of the dental implant. Moreover, the acrylic extension of the RN abutment is very difficult to shape. Drills often become clogged with the material as the material is rather wax-like. Therefore, it is melted into shape instead of ground into shape. Shaping of the acrylic extension tends to be timely, costly, and in some instances frustrating. In addition, the acrylic shaping must be done outside of the mouth to prevent contamination of the surgical site. Once the crown has been fabricated, a hole must be strategically placed in the crown for the tightening wrench to fit. After the crown has been placed and tightened, the screw hole must now be covered with another dental material. This step again adds time and cost. Lastly, the RN abutment itself is costly, adding to the already high cost of acquiring a dental implant.

It is apparent, therefore, that there is a need for a dental prosthesis abutment system that obviates or mitigates at least one of the disadvantages of prior art systems.

SUMMARY OF THE INVENTION

In accordance with one aspect, there is provided a dental abutment system. The dental abutment system may be temporary or permanent.

In accordance with another aspect, there is provided a dental abutment system comprising a cap; at least one retentive member coupled to the cap; and at least one sheath coupled to said at least one retentive member. In another aspect, said at least one sheath is removably coupled to said at least one retentive member. In a further aspect, each of said at least one sheath is removably coupled to a respective one of said at least one retentive member. In still another aspect, said at least one sheath is slidably coupled to said at least one retentive member. In another aspect, said at least one sheath covers said at least one retentive member. In a further aspect, said at least one sheath comprises an inner surface and an outer surface, the outer surface comprising a greater friction than the inner surface. In another aspect, said at least one sheath comprises an inner surface and an outer surface, the inner surface comprising a greater friction than the outer surface.

In other aspects, the cap is a healing cap. In another aspect, the cap is adapted for coupling to a dental implant; in yet other aspects, the cap is adapted for operative coupling to the dental implant; in other aspects, the cap comprises a socket for coupling the cap to the dental implant; in other aspects, the cap comprises a shaped periphery that is adapted to engage a sloped periphery of the dental implant; in other aspects, the shaped periphery comprises a downward turned lip; in other aspects, said at least one retentive member and said at least one sheath are adapted to receive a dental prosthesis; in other aspects, the dental prosthesis is removable from said at least one retentive member such that said at least one sheath decouples from said at least one retentive member with the dental prosthesis; in other aspects, the dental prosthesis is removable from said at least one retentive member such that said at least one sheath remains coupled to said at least one retentive member; in further aspects, said at least one retentive member is a member capable of receiving and retaining the dental prosthesis; in other aspects, said at least one sheath is made from a resilient material; in other aspects, said at least one retentive member comprises at least one area-of-weakness for facilitating the breaking of said at least one retentive member under application of an excess force to said at least one retentive member; in yet other aspects, said at least one retentive member is substantially orthogonal to the cap; in another aspect, said at least one retentive member is integral with the cap.

In another aspect, there is provided a system comprising the dental abutment system, said dental abutment system being coupled to a dental implant and/or a dental prosthesis. In other aspects, said dental abutment system is permanently or temporarily coupled to the dental implant and/or the dental prosthesis; in other aspects, the cap is coupled to the dental implant; in further aspects, the cap comprises a shaped periphery that is adapted to engage a sloped periphery of the dental implant; in other aspects, the shaped periphery comprises a downward turned lip; in other aspects, said at least one retentive member and said at least one sheath are adapted to receive the dental prosthesis; in other aspects, the dental prosthesis is removable from said at least one retentive member such that said at least one sheath decouples from said at least one retentive member with the dental prosthesis; in other aspects, whereby the dental prosthesis is removable from said at least one retentive member such that said at least one sheath remains coupled to said at least one retentive member; in other aspects, the dental prosthesis comprises at least one bore; the dental implant comprises at least one bore; and the cap comprises a shaft, wherein the shaft is coupled to said at least one bore of the dental implant and said at least one bore of the dental prosthesis is coupled to said at least one sheath coupled to said at least one retentive member; in other aspects, the dental prosthesis comprises a provisional crown or a permanent crown.

In another aspect, there is provided a healing cap comprising a surface and at least one retentive member for receiving a dental prosthesis, said at least one retentive member being coupled to the surface and said at least one retentive member comprising an area-of-weakness. In further aspects, the area-of-weakness facilitates decoupling of said at least one retentive member when an excess force capable of causing damage to a dental implant is applied; in other aspects, the area-of-weakness comprises a coupling interface between said at least one retentive member and the surface, wherein the coupling interface is a structural point-of-weakness; in other aspects, said at least one retentive member is substantially orthogonal to the surface; in other aspects, the surface is a substantially annular surface.

In further aspects, there is provided a method comprising: coupling the dental abutment system to a dental implant. In other aspects, the dental abutment system is permanently coupled to or temporarily coupled to the dental implant; in yet another aspect, the method further comprises coupling a dental prosthesis to said at least one sheath coupled to said at least one retentive member; in other aspects, coupling the dental prosthesis to said at least one sheath coupled to said at least one retentive member comprises slidably coupling the dental prosthesis to said at least one sheath coupled to said at least one retentive member; in other aspects, the method further comprises removing the dental prosthesis from said at least one sheath coupled to said at least one retentive member; in other aspects, said at least one sheath decouples from said at least one retentive member with the dental prosthesis; in other aspects, said at least one sheath remains coupled to said at least one retentive member; in further aspects, the method further comprises re-coupling the dental prosthesis or another dental prosthesis to said at least one retentive member, wherein the dental prosthesis or the other dental prosthesis is permanently coupled to or temporarily coupled to the dental implant; in other aspects, re-coupling comprises slidably coupling the dental prosthesis or said other dental prosthesis to said at least one retentive member; in other aspects, re-coupling the dental prosthesis follows re-shaping of the dental prosthesis and/or polishing of the dental prosthesis.

In yet another aspect, there is provided a kit comprising the system described above and instructions for use.

In accordance with another aspect, there is provided a dental abutment system comprising: a healing cap; at least one retentive member coupled to the healing cap; and at least one sheath removably coupled to said at least one retentive member. In another aspect, at least one sheath is slidably coupled to said at least one retentive member. In a further aspect, the healing cap is coupled to a dental implant. In an additional aspect, the abutment system is associated with a dental prosthesis.

In accordance with a further aspect, there is provided a dental prosthesis system comprising: a dental prosthesis comprising at least one bore; a dental implant comprising at least one bore; and a dental abutment system comprising a shaft and at least one sheath covered retentive member, wherein the shaft is coupled to said at least one bore of the dental implant and said at least one bore of the dental prosthesis is coupled to said at least one sheath covered retentive member. In a further aspect, each of the at least one sheath covered retentive pin comprises a sheath slidably coupled to a retentive member.

In accordance with another aspect, there is provided a healing cap comprising a surface and at least one retentive member for receiving a dental prosthesis, said at least one retentive member being coupled to the surface and said at least one retentive member comprising a structural point-of-weakness. In another aspect, the structural point-of-weakness facilitates decoupling of said at least one retentive member when an excess force capable of causing damage to a dental implant is applied. In a further aspect, the at least one retentive member is substantially orthogonal to the surface. In yet another aspect, the surface is a substantially annular surface. In still a further aspect, the structural point-of-weakness comprises a coupling interface between said at least one retentive member and the surface.

In accordance with yet another aspect, there is provided a method for temporizing a dental prosthesis, the method comprising: coupling a dental abutment system to a dental implant, the dental abutment system having at least one retentive member; coupling at least one sheath to said at least one retentive member; and coupling the dental prosthesis to said at least one sheath coupled to said at least one retentive member. In a further aspect, coupling the at least one sheath to the at least one retentive member comprises slidably coupling the at least one sheath to the at least one retentive member.

The novel features of the present invention will become apparent to those of skill in the art upon examination of the following detailed description of the invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention and claims that follow.

BRIEF DESCRIPTION OF THE DRAWINGS

Certain embodiments of the present invention will now be described more fully with reference to the accompanying drawings, wherein like numerals denote like parts.

DETAILED DESCRIPTION OF THE EMBODIMENTS

In the following description, at least one embodiment of a cap, a dental abutment system, a system comprising the abutment system, and a method of using the same is provided. In a specific embodiment, the dental abutment system comprises a cap, at least one retentive member coupled to the cap, and at least one sheath coupled to the at least one retentive member.

In an embodiment of a method using the dental abutment system, a temporary dental prosthesis, such as a provisional crown, is placed over one or more sheaths, such that the sheaths facilitate the removal of the dental prosthesis from the retentive member(s) of the abutment system.

Figure 1A:
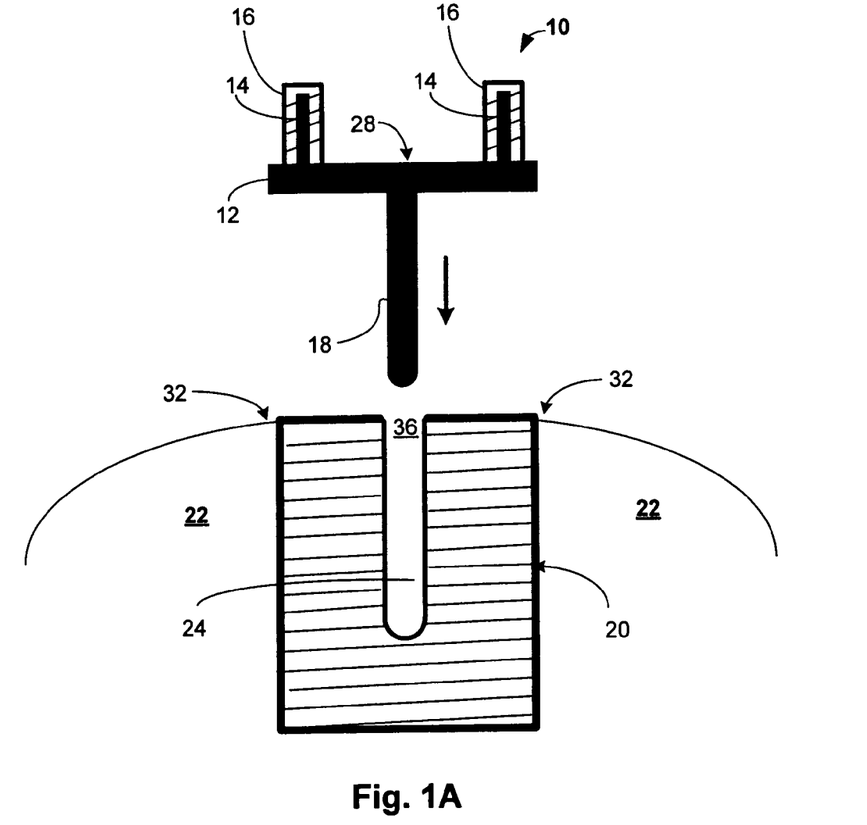
FIG. 1A is a side view, in partial cross-section, of one embodiment of an abutment system and dental implant.

Turning now to FIG. 1A, one embodiment of a dental abutment system 10 is shown. The system 10 comprises a cap 12, a pair of retentive members 14 coupled to the cap 12, a pair of sheaths 16 removably coupled to the retentive members 14, and an elongate threaded shaft 18 for securing the abutment system 10 to a surgically placed dental implant 20 into a jaw bone 22. As illustrated, the dental implant 20 comprises a threaded bore 24 that is adapted to receive and secure the elongate threaded shaft 18 to the surgically placed dental implant 20. Retentive members 14, which protrude upwardly from the surface of the cap 12, are adapted to receive and retain either a temporary dental prosthesis 26 (e.g., provisional crown) or a permanent dental prosthesis (not shown in this Figure).

The embodiment of FIG. 1A may have one or more retentive members and correspondingly, one or more sheaths.

Although the threaded shaft 18 is utilized for securing the abutment system 10 to the dental implant 20, any suitable approach for coupling the abutment system 10 to the dental implant 20 contemplated by one skilled in the dental arts may be used. Moreover, any suitable dental implant may be used for coupling to the abutment system 10.

Figure 1B:
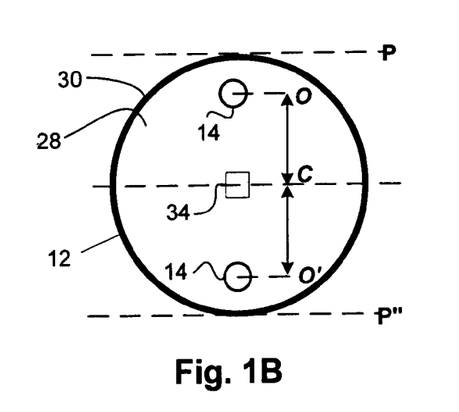
FIG. 1B is a top plan view of a cap of FIG. 1A.

FIG. 1B shows a top plan view of the cap 12 of FIG. 1A. The cap 12 comprises an annular surface 28 having an outer periphery 30, where the outer periphery 30 is shaped to promote the healing of gingival tissue 32 surrounding dental implant 20. Cap 12 further provides a sufficiently tight seal between the threaded bore 24 of the dental implant 20 and the oral environment for minimizing the risk of infection. During an implant procedure, the abutment system 10 is coupled to dental implant 20 by, for example, screwing the elongate threaded shaft 18 of the abutment system 10 into the threaded bore 24 of the dental implant 20. It is appreciated that although dental implant 20 and abutment system 10 are coupled via matched screw threads, other techniques and methods of inserting and securing an abutment system to an implant may be developed or used as contemplated by one skilled in the dental arts. For example, an epoxy type material may be used to couple an elongate shaft within a bore.

Figure 2:
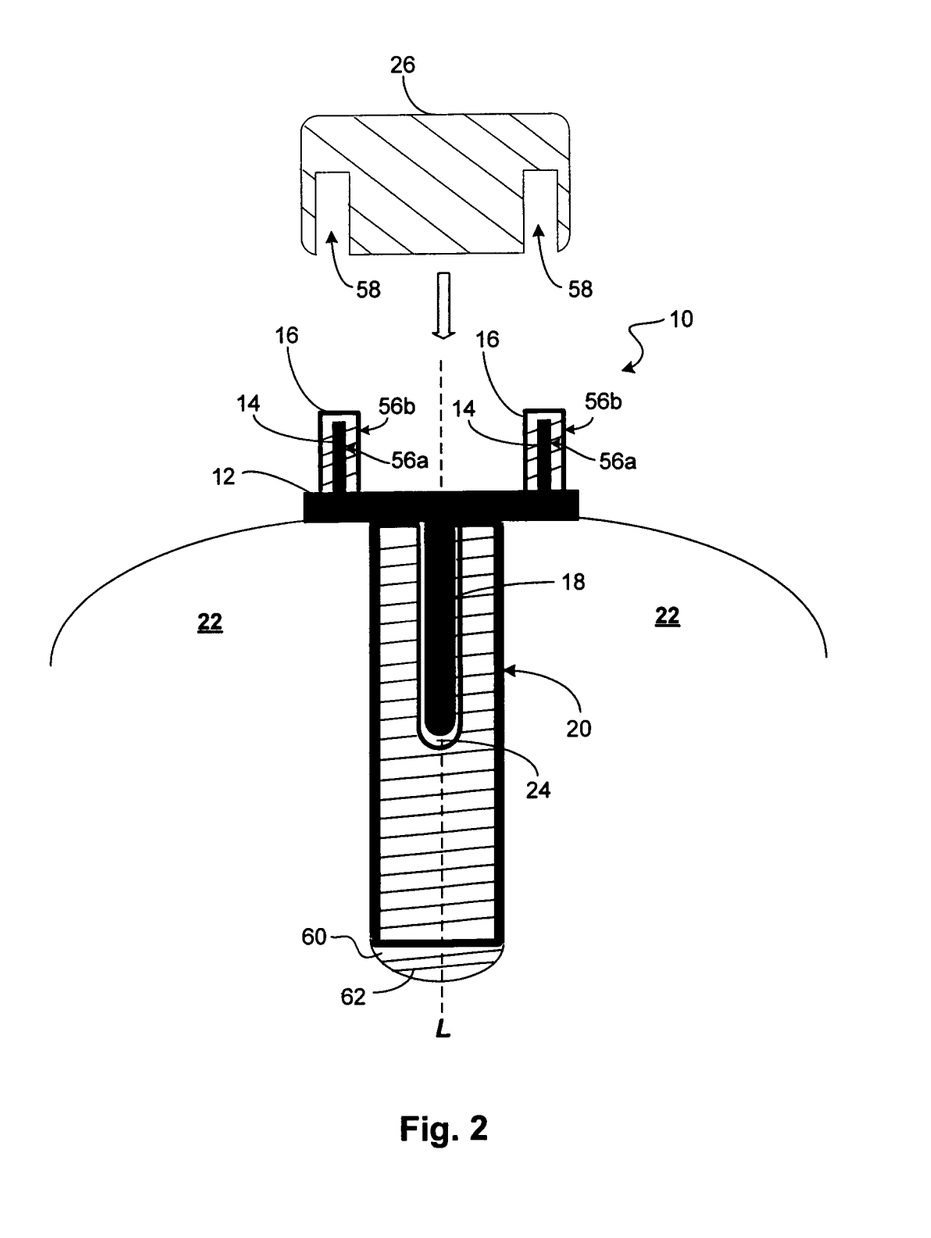
FIG. 2 is a side view, in partial cross-section, of the abutment system of FIG. 1A coupled to the dental implant and a dental prosthesis aligned with the abutment system.

Referring to FIGS. 1A and 1B, a socket 34 is located in the center of the surface 28 for facilitating the coupling of abutment system 10 to the dental implant 20. As illustrated, the elongate threaded shaft 18 is positioned at opening 36 of the threaded bore 24. A complementary driving tool (not shown) is coupled to the socket 34 for rotatably driving the elongate threaded shaft 18 into the threaded bore 24 of the dental implant 20. The elongate threaded shaft 18 is driven into the threaded bore 24 until the planar surface of the cap 12 seals the opening 36 of the threaded bore 24. The final position of the abutment system 10 relative to the dental implant 20 is shown in FIG. 2.

In general, the cap 12 is typically made of materials that are biocompatible. The cap described throughout is, typically, a healing cap but can be any suitable cap. The cap 12 is also typically made of mechanically suitable materials that can withstand normal forces of mastication without bending, fracturing or otherwise becoming mechanically deformed. Suitable materials may comprise, but are not limited to, metals like titanium, titanium alloys, cobalt, cobalt alloys, stainless steel or high noble metals or alloys. The outer periphery 30 of the surface 28 may be shaped to promote the healing of the gingival tissue following the surgical placement of the dental implant 20 and provide a sufficiently tight seal between dental implant 20 and the oral environment for the prevention of infection.

As previously described, socket 34 (FIG. 1B) may be formed from an indent in the surface 28. However, it will be appreciated that socket 34 may be formed from a protrusion located on the top surface of cap 12, whereby the protrusion is adapted to receive a complementary driving tool for securing the cap 12 to the dental implant 20. Furthermore, although it has been described that the coupling between the elongate threaded shaft 18 and threaded bore 24 is accomplished using a rotational coupling arrangement effectuated by a complementary driving tool acting on socket 34, the cap 12 may be secured to the dental implant 20 using any known coupling arrangement, such as but not limited to, a press-fit arrangement (not shown).

Figure 1C:
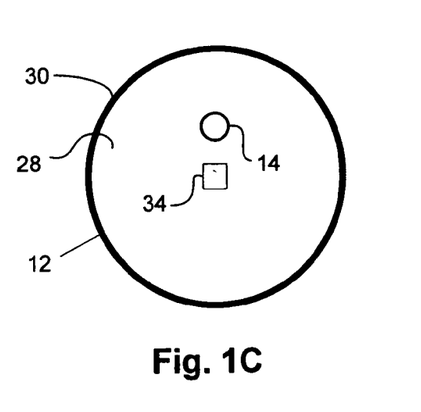
FIG. 1C is a top plan view of another embodiment of a cap.

Turning now to FIG. 1C, an alternative embodiment of the cap 12 is shown, where a single retentive member 14 is coupled to the cap 12 which provides sufficient strength for securing a dental prosthesis in place. In such an embodiment, a dental prosthesis is secured in place by a single retentive member 14. It will be appreciated that the placement of the socket 34 is not restricted to the position on the cap 12 as depicted in FIG. 1C and that the socket 34 and a single retentive member, for example, may be formed out of a combined member that secures a dental prosthesis in place and effectuates the coupling of a cap to a dental implant.

Depending on the position of a dental implant within the mouth, a dental prosthesis replacing a natural tooth may have different strength requirements with respect to being coupled to one or more retentive members 14. For example, a cap may be coupled to three or more retentive members 14. Further, in some aspects, the minimum or maximum number of retentive member(s) 14 may be determined by accessibility to socket 34 by the complementary driving tool. For example, if the number of retentive members is selected to be more than a certain number, placement of the complementary driving tool for sufficiently tightening the cap 12 may be restricted. However, as mentioned above, other suitable approaches may be used to couple the cap 12 to the dental implant 20. Therefore, one or more retentive members may be used.

Retentive members 14 may have a length ranging from about 1-10 mm and a diameter ranging from about 0.25 to 2.00 mm. However, based on different applications and conditions, the dimensions of retentive members 14 may be altered by the surgical specialist during a dental procedure. As depicted, the retentive members 14 are integral with the cap 12 by, for example, being machined as a single unit. However, it will be appreciated that retentive members 14 may not be integral with the cap 12 and thus may be a separate component capable of being coupled to the cap 12 using various techniques. For example, retentive members 14 may be coupled with any standard cap by bonding, laser welding, mechanical threading, or various chemical methods such as gluing with epoxy or polymers. Each of the retentive members 14 may comprise outer surfaces that are smooth for facilitating the placement of the sheath(s) or outer surfaces that are textured (e.g., rough surface, threaded surface, distributed surface protrusions) for providing increased retention of the sheath(s) when slidably placed over the retentive members 14. Although, as shown in FIGS. 1B and 1C, the cross-section of the retentive members 14 and the sheaths 16 are substantially circular (i.e., circle or ellipse), it will be appreciated that any suitable cross-section shape may be adopted for the retentive members and the sheaths, reducing manufacturing costs, and increasing the retentive ability of the sheaths.

Depending on the coupling techniques used to couple retentive members 14 to the surface 28 of the cap 12, the retentive members 14 may be removed in favor of conventionally attaching a dental prosthesis directly to the surface 28 of the cap 12. The ability to removably attach retentive members 14 further provides an opportunity to utilize different retentive members having various characteristics (e.g., length, diameter, material, etc.).

Generally, an area-of-weakness may comprise the purposeful incorporation of one or more points or a region that is adapted to fracture or break based on the application of an applied force or range of forces that exceed a given threshold. The retentive members 14 may also be constructed to have such an area of weakness, which permits the retentive members 14 to break-away from the cap 12 in the event that excessive force is experienced by the dental prosthesis 26 (FIG. 3) during mastication. For example, an excessive force may cause the displacement of the dental implant 20 in relation to the jaw bone 22, thereby jeopardizing the osseointegration of the dental implant 20. The controlled breaking-away of the retentive members 14 ensures that excessive force is not transferred from the dental prosthesis 26 to the dental implant 20 via the cap 12. An area of weakness may be created at a point-of-contact between an end of the retentive members 14 and the surface 28. However, the application of other suitable locations on the retentive members 14 for creating an area-of-weakness may also be contemplated.

Figure 1D:
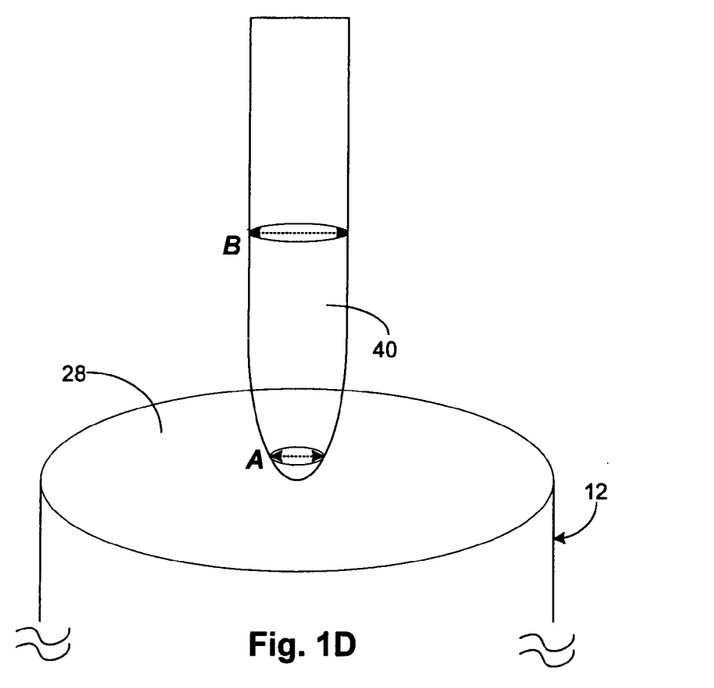
FIG. 1D is a side view of an embodiments of a retentive members.
Figure 1E:
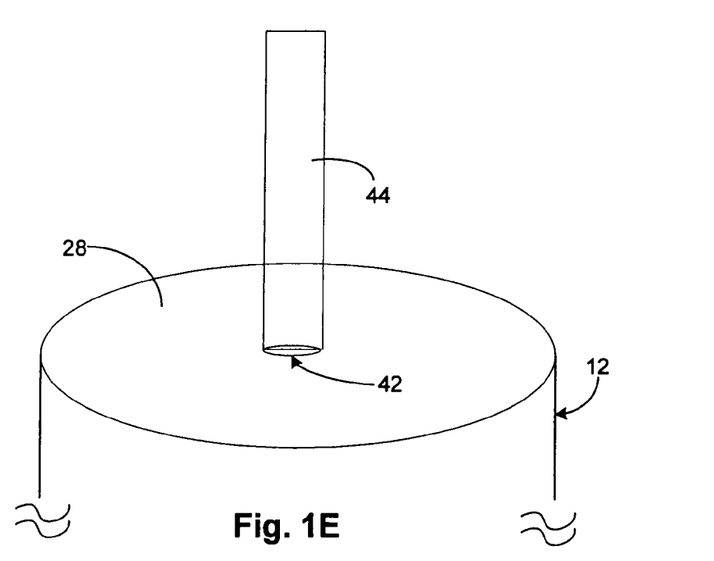
FIG. 1E is a side view of another embodiment of a retentive member.

Turning now to FIG. 1D, in one aspect where a retentive member 40 is an integral part of the cap 12, an area-of-weakness may be created by providing a reduced diameter A in the region of the point of contact of the retentive member 40 with the surface 28 relative to an increased diameter B at the upper portion of the retentive member 40. In another aspect, as shown in FIG. 1E, the strength of a coupling region 42 (e.g., bonding, welding, or threading location) between a coupled retentive member 44 and the cap 12 is set to be slightly less than an excess force capable of causing sufficient micromovement in the dental implant 20 to impair the osseointegration process.

Figure 1F:
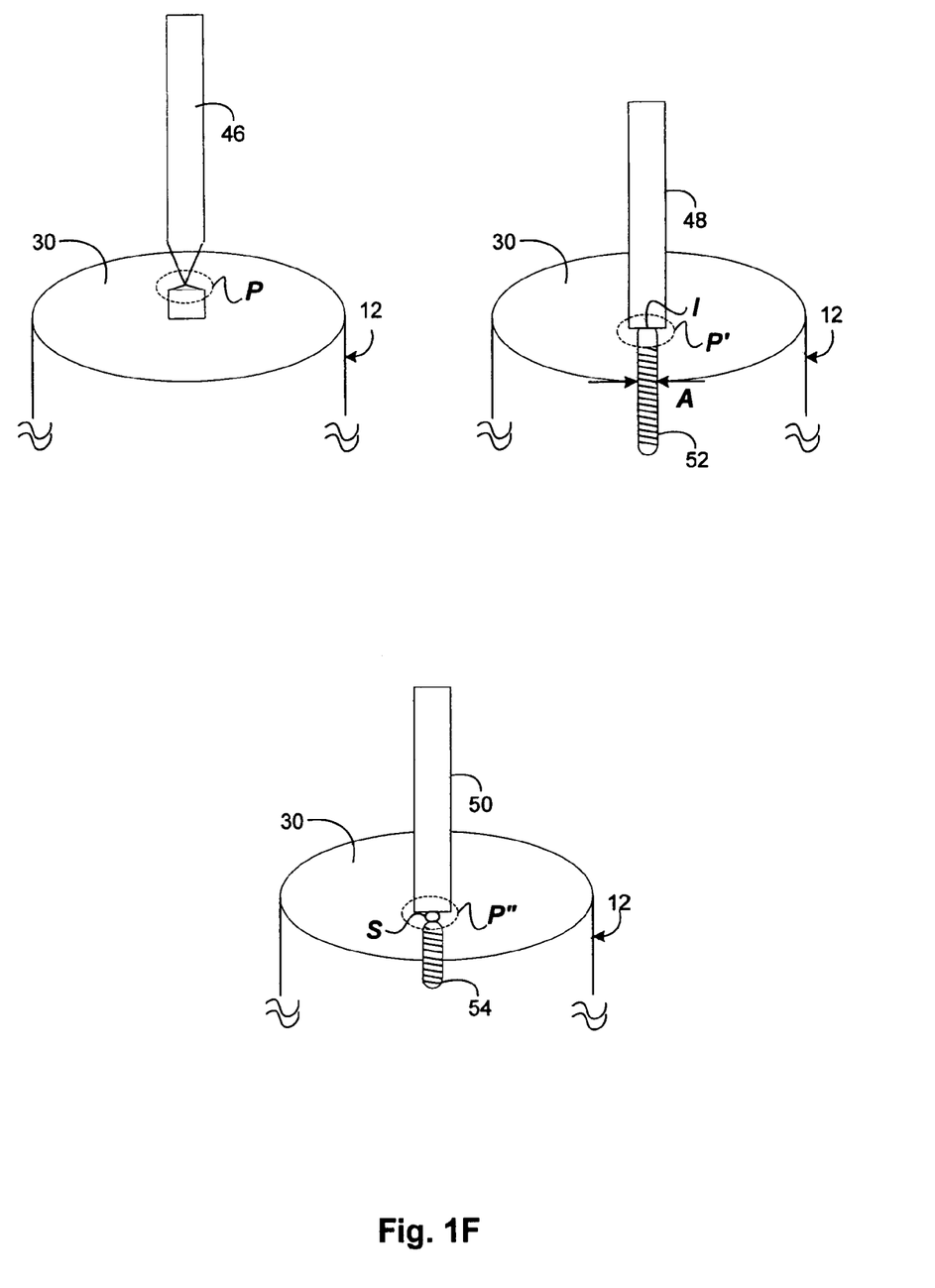
FIG. 1F is a side view of another embodiment of a retentive member.

As shown in FIG. 1F, other areas-of-weakness may be incorporated by applying different shaping techniques to or along retentive members 46, 48, and 50. Accordingly, by controllably including a point-of-weakness in the retentive members 46, 48 and 50 or at their respective point of contact with surface 28, implant failure resulting from the excess micromovement of the dental implant 20 may be avoided. For example, as illustrated, an area-of-weakness P may be created by reducing the cross section of retentive member 46 in a region close to the surface 28. Similarly, an area-of-weakness P' may be created by coupling a threaded screw 52 of cross-sectional area A to retentive member 48, whereby the threaded screw 52 is adapted to couple retentive member 48 to surface 28. In such an aspect, by controlling the cross-sectional area A of a threaded screw 52, an area-of-weakness P' may be created at, or in close proximity to, a coupling interface I between the threaded screw 52 and the retentive member 48. For example, in another aspect, a spherical attachment S acts as an interface between a retentive member 50 and a threaded screw 54. By controlling the diameter and/or material of spherical attachment S, the required break-away force corresponding to the area-of-weakness P''' may also be controlled.

Referring to FIG. 1B, retentive members 14 are illustrated as being substantially symmetrically displaced relative to the center of surface 28, as indicated by OC=CO'. However, retentive members 14 may be positioned about the center of surface 28 in an asymmetric manner. For example, both retentive members 14 may be placed (not shown) within the same semi-circular region of the surface 28 between axes O and C, or alternatively, between axes C and O'.

Turning now to FIG. 2, the sheaths 16 are adapted to substantially cover the retentive members 14. In order to facilitate the placement and removal of the dental prosthesis 26 from the cap 12, the inner surfaces 56a of the sheaths 16 are received by and frictionally engage the retentive members 14. In one aspect, the outer surfaces 56b of the sheaths 16 exhibit greater friction against the surfaces of the prosthesis bores 58 in comparison to the friction exhibited between the inner surfaces 56a of the sheaths 16 and the retentive members 14. Accordingly, during coupling of the dental prosthesis 26 to the cap 12, the bores 58 of the dental prosthesis 26 receive and engage the sheaths 16 and the retentive members 14. However, upon removal of the dental prosthesis 26 from the cap 12, the sheaths 16 remain embedded within the bores 58 of the dental prosthesis 26 as a result of the greater friction exhibited between the bores 58 and the outer surfaces 56b of the sheaths 16. According to another aspect, the inner surfaces 56a of the sheaths 16 may exhibit greater friction against the retentive members 14 than that exhibited between the outer surfaces 56*b* and the surfaces of the bores 58. Thus, upon removal of the dental prosthesis 26 from the cap 12, the sheaths 16 remain attached to the retentive members 14 as a result of the greater friction exhibited between the retentive members 14 and the inner surfaces 56*a* of the sheaths 16.

Although, the sheaths 16 have been depicted as almost entirely covering the retentive members 14, it will be appreciated that the sheaths 16 need only cover a portion of the retentive members 14. As shown in the Figures, each of the retentive members 14 is adapted to engage a respective bore 58 formed within the dental prosthesis 26. Each member in the pair of retentive members 14 is substantially parallel to the other member and to the longitudinal centre axis L of the cap 12. The retentive members 14 are also orientated to be substantially orthogonal to the surface 28 for facilitating the coupling and decoupling of the dental prosthesis 26 with respect to the cap 12.

In an embodiment, there is a method utilizing the abutment system 10. The method comprises coupling the dental abutment system to a dental implant. In another embodiment, the method comprises coupling a dental prosthesis to the dental abutment system. The dental abutment system may be permanently coupled to or temporarily coupled to the dental implant and/or dental prosthesis.

Figure 3:
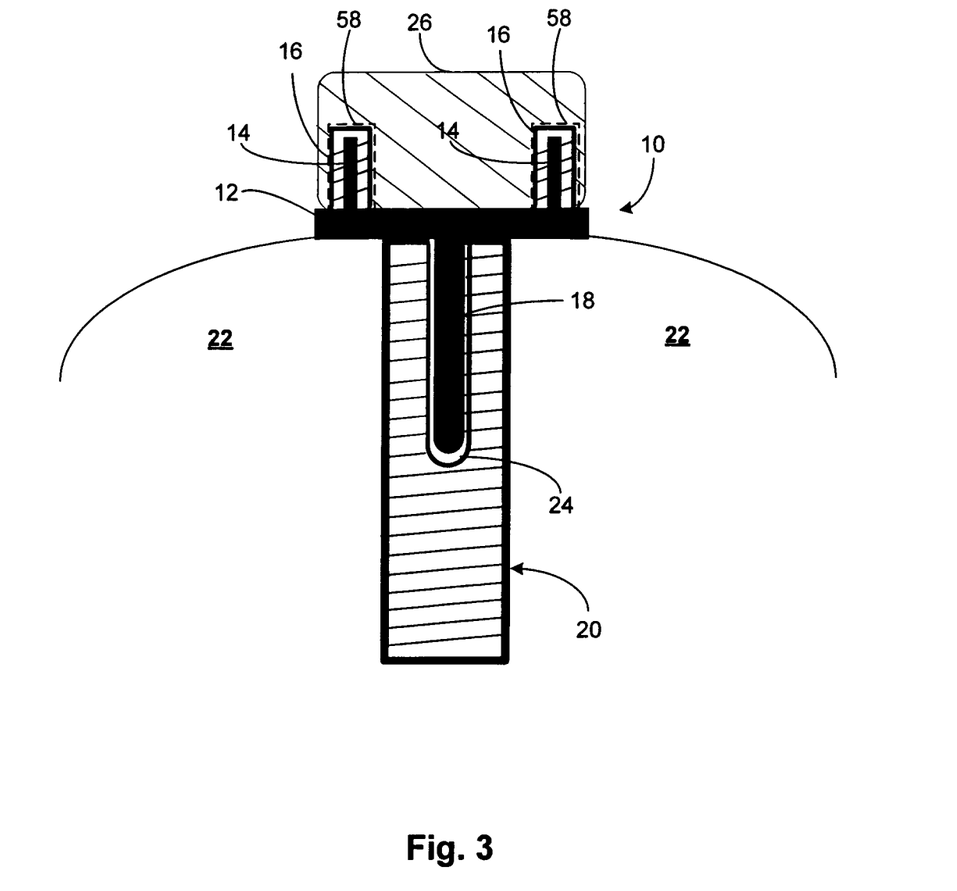
FIG. 3 is a side view, in partial cross-section, of the abutment system of FIG. 1A coupled to the dental implant and the dental prosthesis of FIG. 2.
Figure 4:
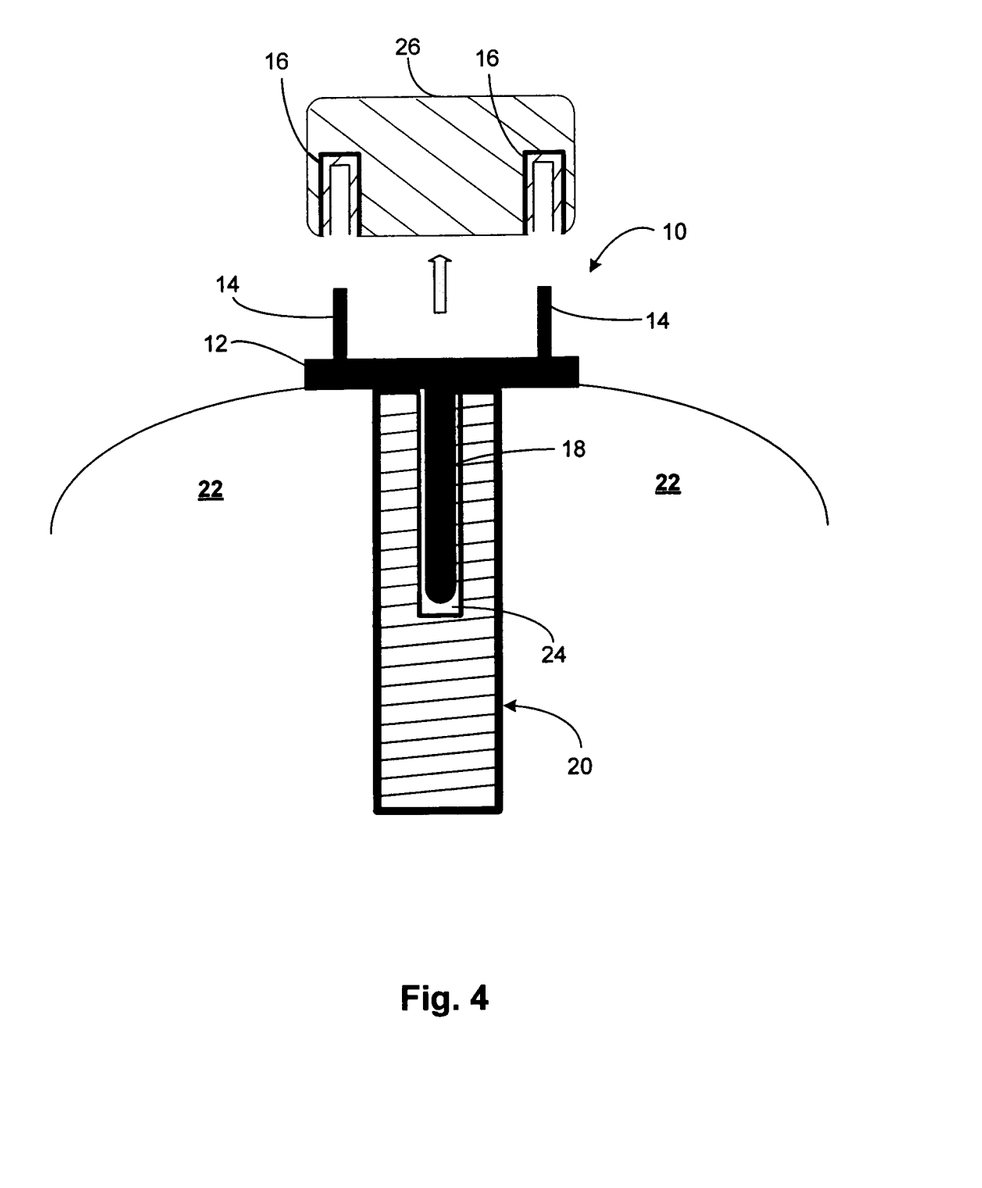
FIG. 4 is a side view, in partial cross-section, of the abutment system of FIG. 1A coupled to the dental implant with the dental prosthesis removed with sheaths.

Turning now to FIGS. 2-4, according to one aspect, a method is provided. Initially, the process comprises drilling an implantation hole 60 into the jaw bone 22 in the region or area of a missing tooth. Implantation hole 60 is generally formed with internal threads 62 which are adapted to receive and engage the threaded bore 24 associated with dental implant 20. Following the placement of dental implant 20 within implantation hole 60, the abutment system 10 is coupled to the dental implant 20 by aligning and screwing the threaded elongate shaft 18 into the threaded bore 24 of dental implant 20. According to known procedures, a conventional temporary impression of the pre-existing dentition is made. Using this temporary impression, a technical specialist is able to create dental prosthesis 26 outside of the mouth.

Referring to FIG. 2, the attachment of the dental prosthesis 26 to the abutment system 10 is accomplished by aligning and coupling the prosthesis bores 58 of the dental prosthesis 26 to the sheath 16 covered retentive members 14.

Referring to FIG. 3, as the dental prosthesis 26 is pushed down onto the retentive members 14, the sheaths 16 covering the retentive members 14 slide-up into the openings within the prosthesis bores 58. During this stage of the temporization procedure, the surgical specialist may need to repeatedly remove the dental prosthesis 26 from the abutment system 10 and the patient's mouth in order to re-shape and polish the dental prosthesis 26 for test fittings associated with the cavity formed by the missing tooth (teeth).

Turning now to FIG. 4, as the dental prosthesis 26 is removed from the retentive members 14 in order to, for example, re-shape and/or polish the dental prosthesis 26, the sheaths 16 remain coupled to the bores 58. This allows the dental prosthesis 26 to be slidably removed from the retentive members 14 using a reduced force. As previously described, the placement and removal, especially repeatedly, of the dental prosthesis 26 from the retentive members 14 of the abutment system 10 may cause unwanted movement and damage to the dental implant 20. Moreover, during removal or placement, the use of excess force on the dental prosthesis 26 may also potentially chip or damage it. Thus, during each placement and removal, the dental prosthesis 26 is easily attached and detached from the abutment system 10 based on the sheaths 16 acting as a buffering layer that provides a smooth sliding interface between the retentive members 14 and the dental prosthesis 26. Once the dental prosthesis 26 is suitably shaped and/or polished, standard temporary dental cement is directly applied to the retentive members 14 for cementing the dental prosthesis 26 to the cap 12. The duration of the temporary cementing of the dental prosthesis 26 to the retentive members 14 may be equivalent to the time interval required for osseointegration of the dental implant 20 within the jaw bone 22.

Upon osseointegration between dental implant 20 and the jaw bone 22, the restorative stage of the temporization procedure begins with the removal of the dental prosthesis 26 from cap 12. At this restorative stage, care should be taken during the removal of the dental prosthesis 26 in order to avoid inflicting excess force capable of dislodging the osseointegrated dental implant.

Without being limited to a particular theory, standard temporary dental cement expands upon hardening for promoting the fixation of the components being cemented together. On this basis, if temporary dental cement is applied directly between retentive members 14 and the prosthesis bores 58 (i.e., without sheaths 16), the expansion and hardening of the temporary cement within the bore 58 may strongly inhibit the subsequent removal of dental prosthesis 26. This in turn is likely to require the use of excess force during the prosthesis removal process and, thus, present a risk of disturbing the surgically placed dental implant 20. However, the buffering or interface layer provided by sheaths 16 facilitates the slidable removal of dental prosthesis 26 from retentive members 14 despite this characteristic of the applied dental cement. The sheaths 16 achieve this as a result of their characteristic elasticity, which cause the sheaths 16 to flexibly deform against the expanding cement. Thus, although the application of the cement creates an increased coupling between dental prosthesis 26 and retentive members 14, the sheaths 16 provide a buffer mechanism for successfully removing the prosthesis without damaging the actual dental implant 20.

When the dental prosthesis 26 is removed from the retentive members 14 and cap 12, the surgical specialist is able to access slot 34 (FIG. 1B) for unscrewing the abutment system 10 from the dental implant 20. Once the abutment system 10 is removed and the cap 12 no longer seals entry to the threaded bore 24 (FIG. 1), a permanent abutment for a permanent dental prosthesis may be secured to the dental implant 20.

Figure 5A:
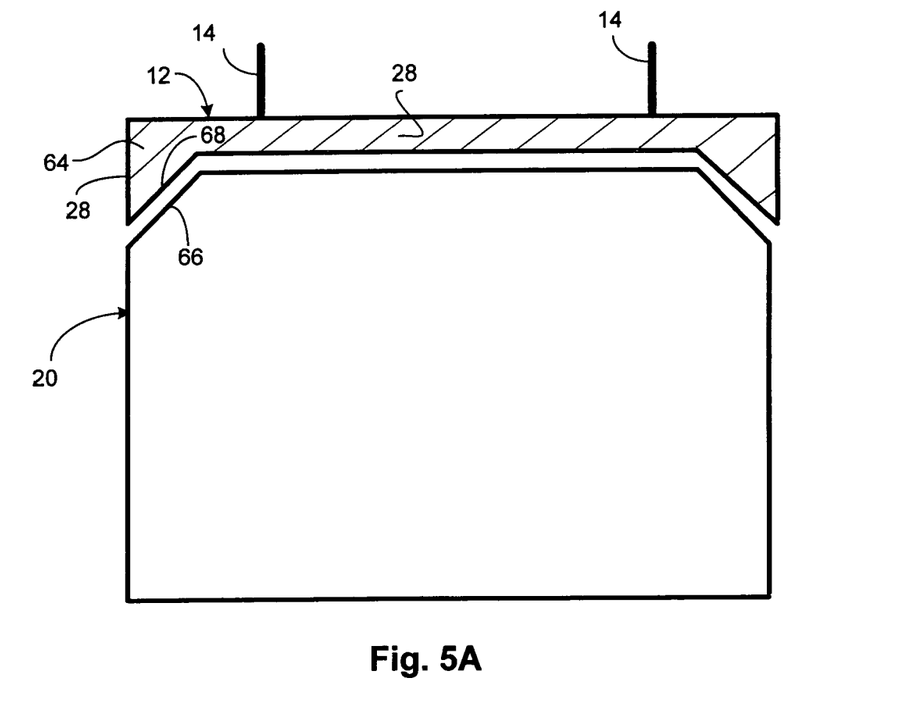
FIG. 5A is a side view, in partial cross-section, of a further embodiment of a cap coupled to a dental implant.

Turning now to FIG. 5A, in one aspect, outer periphery 30 of surface 28 is formed with a downward turned lip 64 that sealingly engages a sloped periphery 66 on the dental implant 20. The angular orientation of surface 68 of the downward turned lip 64 and the sloped periphery 66 on the dental implant 20 promote both the above-mentioned expedited healing of gingival tissue (not shown in this Figure) and the increased sealing criteria.

Figure 5B:
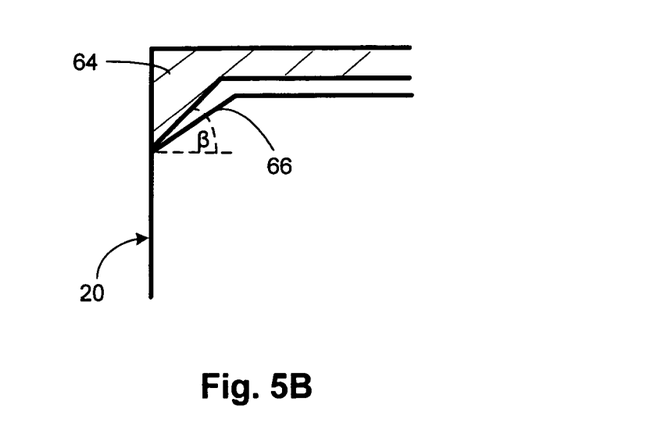
FIG. 5B is a side view, in partial cross-section, of yet another embodiment of a cap coupled to a dental implant.

Turning now to FIG. 5B, in other aspects, the downward turned lip 64 may comprise a steeper slope (angle $\beta$) than sloped periphery 66. In this arrangement, the increased slope of downward turned lip 64 relative to sloped periphery 66 permits an even tighter seal between cap 12 and dental implant 20.

Abutment system 10 may be utilized with a dental prosthesis that is either temporary or permanent. A temporary dental prosthesis (i.e., provisional crown), may be constructed from acrylic or similar materials. Other suitable materials, such as polyurethane, methyl methacrylate, or resin may also be used. In one embodiment, it may be possible to produce a permanent crown that permanently attaches to abutment system 10 without the need for the additional step of removing abutment system 10 during the restorative stage of the temporization procedure. The permanent crown is constructed from more durable material such as milled porcelain.

Although abutment system has been described as comprising a cap, retentive member(s), and sheath(s), the abutment system need not be packaged as a complete integral assembly. Thus, the cap, retentive member(s), and sheath(s) may be discrete components (e.g., a kit of constructible parts) that are efficiently assembled by, for example, a surgical specialist to form the abutment system. The abutment system may also be conveniently modified by a technician or surgical specialist to be a standard cap for use in conventional dental implantation procedures by removing the retentive member(s) using conventional tools. Furthermore, as illustrated and described herein, the retentive members may also comprise threaded screws that allow them to be rotatably coupled to a variety of separately acquired caps.

Although the abutment system, or components of the abutment system, may be manufactured by any method, in one embodiment, the abutment system (comprising a healing cap and retaining member(s), for example) may be manufactured as a single integrated piece using "computer-aided design/computer-aided manufacturing" (CAD/CAM) technology. In another embodiment, one or more components of the abutment system may be manufactured individually and separately using CAD/CAM technology. In yet another embodiment, the abutment system may be reshaped for fitting as a single integrated piece using CAD/CAM technology. In still another embodiment, one or more components of the abutment system may be individually and separately reshaped for fitting using CAD/CAM technology. As is known in the art, CAD/CAM technology is based on the linking of computer aided design software to one or more computer-controlled manufacturing machines, and enables parts to be automatically manufactured based on a design in the form of an electronic drawing. As is also known in the art, a CAD/CAM system may also comprise a subsystem for entering the dimensions of a previously-fabricated part into the system, such as an optical scanner or a camera, for example.

With respect to the abutment system, it may be permanently or temporarily coupled to the dental implant depending on the desired use.

With respect to the retentive member(s), the retentive member(s) may be any suitable member that is capable of receiving and retaining a dental prosthesis. For example, and without being limited thereto, any protrusion such as a pin or a screw may be used. The retentive member(s) are typically made of materials that are biocompatible. Some suitable materials may comprise, but are not limited to, metals like titanium, titanium alloys, cobalt, cobalt alloys, stainless steel or high noble metals or alloys.

With respect to the sheath(s), the sheaths may be made from any suitable materials known in the dental arts. In aspects, the sheath(s) are made from resilient materials, such as, but not limited to, rubbers or plastics. Other resilient materials known in the dental arts may also be contemplated.

When introducing elements disclosed herein, the articles "a", "an", "the", and "said" are intended to mean that there are one or more of the elements. The terms "comprising", "having", "including" are intended to be open-ended and mean that there may be additional elements other than the listed elements.

With respect to the terms "coupled" or "coupling", these terms are understood to encompass integral with or connected thereto.

The description as set forth is not intended to be exhaustive or to limit the scope of the invention. Many modifications and variations are possible in light of the above teaching without departing from the spirit and scope of the following claims. It is contemplated that the use of the present invention can involve components having different characteristics. It is intended that the scope of the present invention be defined by the claims appended hereto, giving full cognizance to equivalents in all respects.

What is claimed is:

1. A dental abutment system comprising:
    a healing cap having a substantially planar and substantially circular cap surface, said cap having a coupling feature at a center of said cap surface shaped to receive a complimentary driving tool;
    at least one retentive member coupled to and extending directly and substantially orthogonally from the cap surface,
    at least one sheath frictionally coupled to and covering said at least one retentive member, wherein each retentive member has a separate sheath frictionally coupled thereto, and wherein each sheath is slidably removable from said retentive member; and
    an elongate shaft extending downwardly from said cap for coupling to a dental implant, said elongate shaft defining a longitudinal axis, the longitudinal axis being generally aligned with the coupling feature at the center of the cap surface,
    wherein said at least at least one retentive member is laterally offset from the coupling feature at the center of the cap surface.

2. The abutment system according to claim 1, wherein said at least one sheath comprises an inner surface and an outer surface, the outer surface comprising a greater friction than the inner surface.

3. The abutment system according to claim 1, wherein the coupling feature is a socket for coupling the cap to the dental implant.

4. The abutment system according to claim 1, wherein the cap comprises a shaped periphery that is adapted to engage a sloped periphery of the dental implant.

5. The abutment system according to claim 4, wherein the shaped periphery comprises a downward turned lip.

6. The abutment system according to claim 1, wherein said at least one retentive member is a member capable of receiving and retaining the dental prosthesis.

7. The abutment system according to claim 1, wherein said at least one retentive member comprises at least one area-of-weakness for facilitating the breaking of said at least one retentive member under application of an excess force to said at least one retentive member.

8. A system comprising a dental abutment system according to claim 1, said dental abutment system being coupled to a dental implant and/or a dental prosthesis.

9. The system according to claim 8, wherein said dental abutment system is permanently or temporarily coupled to the dental implant and/or the dental prosthesis.

10. The system according to claim 8, wherein the cap is coupled to the dental implant.

11. The system according to claim 8, wherein the cap comprises a shaped periphery that is adapted to engage a sloped periphery of the dental implant.

12. The system according to claim 11, wherein the shaped periphery comprises a downward turned lip.

13. The system according to claim 8, wherein the dental prosthesis comprises at least one bore; and the dental implant comprises at least one bore, wherein the shaft is coupled to said at least one bore of the dental implant and said at least one bore of the dental prosthesis is coupled to said at least one sheath coupled to said at least one retentive member.

14. The system according to claim 8, wherein the dental prosthesis comprises a provisional crown or a permanent crown.

15. The system according to claim 1, wherein there are two retentive members and two sheaths.

16. The system according to claim 1, wherein the at least one retentive member is a pin.

17. The abutment system according to claim 1, wherein the coupling feature is a socket or a protrusion.

18. A kit comprising;
- a healing cap having a substantially planar and substantially circular cap surface, said cap having a coupling feature at a center of said cap surface shaped to receive a complimentary driving tool, wherein at least one retentive member is coupled to and directly extends substantially orthogonally from the cap surface;
- at least one sheath for frictionally coupling to and covering said at least one retentive member, wherein each retentive member has a separate sheath frictionally coupled thereto, and wherein said at least one each sheath is slidably removable from said retentive member; and
- an elongate shaft extending downwardly from said cap for coupling to a dental implant, said elongate shaft defining a longitudinal axis, the longitudinal axis being generally aligned with the coupling feature at the center of the cap surface,
- wherein said at least at least one retentive member is laterally offset from the coupling feature at the center of the cap surface.

19. The kit according to claim 18, wherein the coupling feature is a socket or a protrusion.

20. A dental abutment system comprising:
- a healing cap having a substantially planar and substantially circular cap surface, said cap having a coupling feature at a center of said cap surface shaped to receive a complimentary driving tool;
- a pair of pins coupled to and extending directly and substantially orthogonally from the cap surface;
- a pair of sheaths, each of said sheaths frictionally coupled to and covering a respective one of said pins, and wherein each of said sheaths is slidably removable from each of said pins; and
- an elongate shaft extending downwardly from said cap for coupling to a dental implant, said elongate shaft defining a longitudinal axis, the longitudinal axis being generally aligned with the coupling feature at the center of the cap surface,
- wherein each of said pins is laterally offset from the coupling feature at the center of the cap surface.

21. The system according to claim 20, wherein each of said pins comprises an area-of-weakness for facilitating the breaking of said pins under application of an excess force to said pins.

22. A system comprising a dental abutment system according to claim 20, said dental abutment system being coupled to a dental implant and/or a dental prosthesis.

23. The system according to claim 20, wherein the coupling feature is a socket or a protrusion.

* * * * *